United States Patent [19]

Klippel

[11] 4,024,874
[45] May 24, 1977

[54] EXTRACTION DEVICE FOR BLOCKED WINDPIPES

[75] Inventor: Allen Pumill Klippel, Clayton, Mo.

[73] Assignee: Rescue Products, Inc., St. Louis, Mo.

[22] Filed: Sept. 30, 1975

[21] Appl. No.: 618,183

[52] U.S. Cl. .............................................. 128/356
[51] Int. Cl.² ........................................ A61B 17/24
[58] Field of Search ................ 128/303 R, 304, 356

[56] References Cited

UNITED STATES PATENTS

| 467,188 | 1/1892 | McShane | 128/304 |
| 839,641 | 12/1906 | Reavley | 128/304 |
| 1,672,816 | 6/1928 | Kohr | 128/304 |
| 1,983,601 | 12/1934 | Conn | 128/304 |
| 2,218,072 | 10/1940 | Runnels | 128/304 |
| 3,581,745 | 6/1971 | Eller | 128/356 |

FOREIGN PATENTS OR APPLICATIONS

| 971,045 | 6/1950 | France | 128/304 |
| 145,701 | 8/1961 | U.S.S.R. | 128/304 |

*Primary Examiner*—Channing L. Pace
*Attorney, Agent, or Firm*—Gravely, Lieder & Woodruff

[57] ABSTRACT

An integral one-piece plastic extraction device for extracting food or other articles from a blocked larynx or windpipe which includes an elongated handle portion and at least one ribbed bowl spoon portion at one free end thereof which is configured, arranged and dimensioned to permit removal of food dangerously lodged in a larynx or windpipe.

3 Claims, 7 Drawing Figures

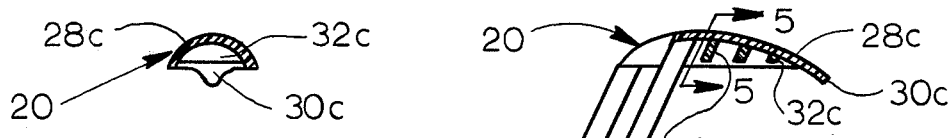
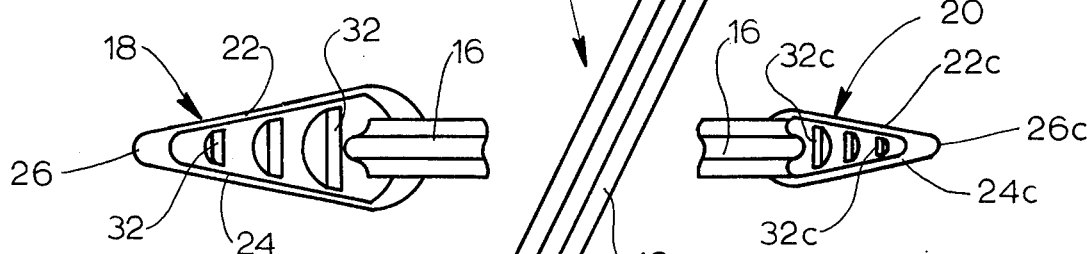
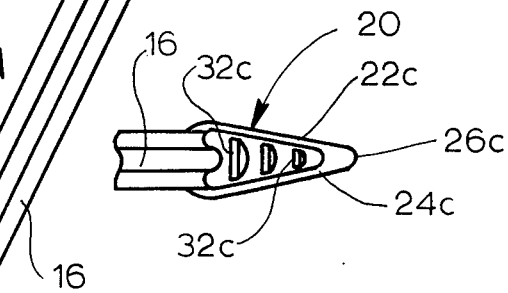
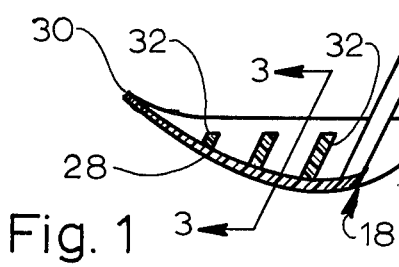
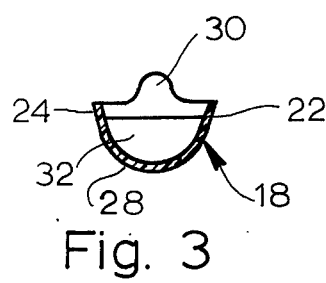
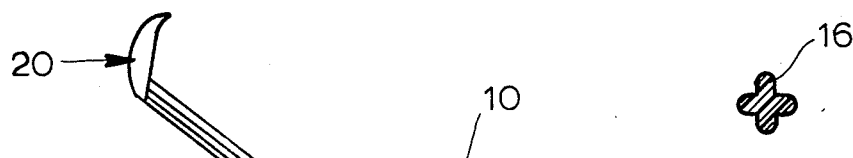
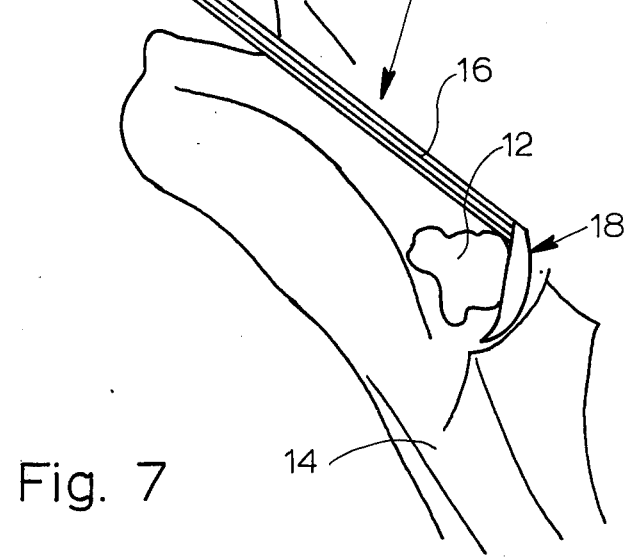

EXTRACTION DEVICE FOR BLOCKED WINDPIPES

SUMMARY OF THE INVENTION

Traditional techniques for removing food obstructions from a larynx or windpipe include slapping a victim on the back and then placing a finger in the victim's throat to remove the obstruction. Sudden death from food choking, commonly known as a "cafe' coronary", is one of the highest common causes of accidental death of humans. It is often mistaken for a heart attack because the victim gasps for breath lost through a food obstruction.

The recent notoriety of "cafe' coronaries" and the difficulty of removing obstructed food by traditional techniques has led to several new proposals including the "Heimlich technique", the use of a "Choke Saver" device, and the use of a vacuum pump deivce. The "Heimlich technique" developed by Dr. Harry J. Heimlich of Cincinnati, Ohio requires pressure being applied to the abdomen of a standing or prone victim to compress residual air in the victim's lungs to increase air pressure in the windpipe or larynx for ejecting the obstructing food, much like popping a cork from champagne bottle. Because it is difficult to hold a human up and squeeze at the same time, this approach is cumbersome and does not prevent the possibility that the food can relodge itself. It also assumes that there always is residual air left in the lungs. The "Choke Saver" device developed by Salvita Corporation of Fort Lauderdale, Florida comprises a pair of curved plastic tweezers about eight inches long. After the curved tweezers are inserted in a victim's throat, the tweezers are squeezed to grip the food obstruction for removal. This device may possibly tear or harm the epiglottis which spans the upper end of the larynx or windpipe, and is limited in design for either adult or child use, but not both in the same device. A vacuum pump device developed by Rockford Safety Equipment Company of Rockford, Illinois establishes a high pressure differential than residual air left in the lungs to withdraw the obstructing food. This device requires the victim's nose passage to be held shut while one of three different sized mouth instruments assembled on the vacuum pump is inserted in the victim's mouth. Difficulty of operation and cost are limiting factors in this approach.

Accordingly, it is an object of the present invention to provide a new and improved device and technique for removing food from blocked windpipes which overcomes the aforementioned difficulties with existing devices and techniques.

More specifically, it is an object of the present invention to provide an economical extraction device for food or other articles to be simply and easily extracted from any human being without damage and without subsequent re-lodging of the obstructing food.

These and other objects and advantages of the present invention are attained by providing an integral one-piece plastic extraction device for food or other article blocked windpipes including an elongated handle portion and ribbed spoon bowl portions at opposite end thereof which are configured, arranged and dimensioned for the average adult at one end and the average child at the other end.

BRIEF DESCRIPTION OF THE DRAWING

FIG. 1 is a side elevational view, partly in section, of the food extraction device which is constructed in accordance with the teachings of the present invention;

FIG. 2 is a fragmentary top plan view of the adult ribbed spoon bowl portion of the food extraction device;

FIG. 3 is an end elevational view of the adult ribbed bowl portion of the food extraction device as taken along line 3—3 of FIG. 1;

FIG. 4 is a fragmentary top plan view of the child ribbed spoon bowl portion of the food extraction device;

FIG. 5 is an end elevational view of the child ribbed bowl portion of the food extraction device as taken along line 5—5 of FIG. 1;

FIG. 6 is a sectional view of the elongated handle portion of the extraction device as viewed along line 6—6 of FIG. 1; and FIG. 7 is a fragmentary side elevational view, partly in section, showing the manner in which the extraction device removes food from an obstructed windpipe.

DESCRIPTION OF THE PREFERRED EMBODIMENTS

The extraction device 10 shown in FIGS. 1 and 7 of the drawing has been developed for extracting food or other articles 12 which block or obstruct a larynx or windpipe 14 as shown in FIG. 7. Food or other articles 12 can sometimes lodge themselves at the uppermost part of the larynx or windpipe 14 in both adults and children as has been explained above. The extraction device 10 has been specifically designed and developed in order that the food or other articles 12 can be safely and quickly removed from the blocked windpipe 14 of either adults or children.

The extraction device 10 is a one-piece molded plastic device made by injection molding techniques. Any suitable plastic material which is strong and durable, so that no parts will be broken during use, may be employed. Cycolac is one such preferred material.

The extraction device 10 comprises an elongated handle portion 16 which is provided at one end with an adult-size ribbed spoon bowl portion 18 and at the other end with a child-size ribbed spoon bowl portion 20. The elongated handle portion 16 is configured in the shape of a rounded cross-shaped design to afford strength while minimizing material usage. Other cross-sectional configurations are, of course, possible.

The elongated handle portion 16 of the extraction device 10 is connected to the ribbed spoon bowl portions 18, 20 for substantially the entire height thereof as will be seen by the manner in which the elongated handle portion 16 at opposite ends thereof extends into and is attached to the ribbed spoon bowl portions 18, 20. This provides supportive strength to the ribbed spoon bowl portions 18, 20 to resist bending or movement thereof relative to the elongated handle portion 16.

Each of the ribbed spoon bowl portions 18, 20 extend from the ends of elongated handle portion 16 in generally opposite direction to each other. It has been discovered that the ribbed spoon bowl portions 18, 20 can scoop into and remove a food obstructed windpipe if the ribbed spoon bowl portions 18, 20 extend at an obtuse angle to the elongated handle portion 16. Preferably, this is in the range of approximately 110°–125°.

Each of the ribbed spoon bowl portions, 18, 20 are similarly constructed, but differ in the size and shape of the elements thereof. It will thus be necessary to describe only one ribbed spoon bowl portions since the same comments apply equally to both except as noted with regard to their different size and shape. The same reference manuals will be used in discribing the elements of both ribbed spoon portions 18, 20 with the suffix c being used to distinguish therebetween.

Reference is made to the adult-size ribbed spoon bowl portion 18 since it is larger and can be more easier visually understood. The ribbed spoon bowl portion 18 includes opposed tapering sidewalls 22, 24 which taper inwardly from the elongated handle portion 16 to a rounded free end portion 26, and a bottom wall 28 which has a shallow curving section extending from the elongated handle portion 16 which terminates in a tip portion 30 that extends above the sidewalls 22, 24 in the vicinity of the rounded free end portion 26 thereof. The ribbed spoon bowl portion 28 also includes a plurality of integral spaced and upstandings ribs 32 which extend upwardly from the inside face of the bottom wall 28 and are connected to the sidewalls 22, 24 as best depicted in FIGS. 1-3. It will be noted that the ribs 32 terminate short of the uppermost portion of the sidewalls 22, 24.

The tapering sidewalls 22, 24 allow the ribbed spoon bowl portion 18 to be inserted into the uppermost portion of the windpipe 14 behind the obstructing article 12 with the tip portion 30 also assisting in wedging itself behind the obstructing article 12. When this has been achieved, the tapering sidewalls 22, 24 and shallow curving bottom wall 28 provide the spoon shape necessary to permit lifting and removal of the obstructing article. The ribs 32 assist in aggressively engaging the obstructing article as the extraction device 10 is removed. The same features are available with the child-size ribbed spoon bowl portion 20 depicted in FIGS. 1 and 4-5 since the only difference is in the size and shape of the various elements making up the child-size ribbed spoon bowl portion 20.

From the foregoing, it will be appreciated that the extraction device of the present invention provides a safe, efficient and economical approach to removing articles from obstructed windpipes.

I claim:

1. An integral one-piece plastic extraction device for food or other article blocked windpipes, comprising an elongated handle portion having each free end thereof being provided with a ribbed spoon bowl portion, said ribbed spoon bowl portions extending in generally opposite directions from the elongated handle portion and at an obtuse angle in a direction away from the middle thereof, each of said ribbed spoon bowl portions having sidewalls that taper convergently from the elongated handle portion to a rounded free end portion and a bottom wall which comprises a shallow curving section extending from the elongated handle portion to a tip portion in the area of juncture with the rounded free end portion, said tip portion extending above the sidewalls of each ribbed spoon bowl portion.

2. The extraction device as defined in claim 1 wherein the ribs of each ribbed spoon bowl portion each extend upwardly from the bottom wall and are connected to the sidewalls of said ribbed spoon bowl portions, said ribs terminating short of the uppermost portions of said sidewalls.

3. The extraction device as defined in claim 1 wherein the elongated hangle portion is connected to each ribbed spoon bowl portion for substantially the entire height thereof.

* * * * *